United States Patent [19]

Bollish et al.

[11] Patent Number: 5,219,330
[45] Date of Patent: Jun. 15, 1993

[54] METHOD AND APPARATUS FOR PREPROGRAMMED INFUSION OF IV MEDICAMENTS

[75] Inventors: Stephen J. Bollish; Robert A. Bramble; Eric L. Firing, all of San Diego, Calif.

[73] Assignee: IMED Corporation, San Diego, Calif.

[21] Appl. No.: 798,937

[22] Filed: Nov. 26, 1991

[51] Int. Cl.$^5$ .......................................... A61M 37/00
[52] U.S. Cl. ..................... 604/53; 604/131; 604/151; 128/DIG. 12
[58] Field of Search ............... 128/DIG. 12, DIG. 13; 604/53, 65, 67, 93, 131, 151–155, 246, 890.1, 891.1, 52

[56] References Cited

U.S. PATENT DOCUMENTS

| | | | |
|---|---|---|---|
| 4,718,576 | 1/1988 | Tamura et al. | 222/63 |
| 4,785,799 | 11/1988 | Schoon et al. | 128/53 |
| 4,889,528 | 12/1989 | Nadai et al. | 604/65 |
| 5,088,981 | 2/1992 | Howson et al. | 604/31 |

OTHER PUBLICATIONS

Hospital Pharmacy, vol. 20, Aug. 1985, entitled "Question: How fast can I taper TPM in a hospital patient?" by Roland N. Dickerson.
"Cyclic Total Parenteral Nutrition" by Katherine McClary Bennett and Gail H. Rosen, Univ. of Maryland Medical Systems, Baltimore, Md.

Primary Examiner—C. Fred Rosenbaum
Assistant Examiner—C. Maslione
Attorney, Agent, or Firm—Nydegger & Associates

[57] ABSTRACT

An apparatus for infusing TPN fluids to a patient includes a source of fluid, a pump for infusing fluid from the source to the patient, and a computer for controlling the operation of the pump. During the operation of the apparatus the infusion rate of the pump is varied according to an infusion regimen that is based on the volume of fluid to be infused and the time during which the fluid is to be infused. This regimen is characterized by a trifurcated ramp up region having interrelated incremental rates of infusion which transition the pump from a zero rate of infusion to a steady state rate of infusion. The infusion regimen is also characterized by a period of steady state infusion which follows the ramp up region, and a ramp down region in which the infusion rate is decremented from the steady state rate based on the remaining volume of fluid to be infused to the patient and the remaining time for infusing this remaining volume of fluid. Infusion rate changes in both the ramp up and ramp down regions is accomplished in steps. Depending on the calculated steady state infusion rate, the step sizes may be either 5 ml/hr or 1 ml/hr. The different time intervals between steps in the ramp up region are related to each other and to the total time for infusing fluids to the patient and the time intervals between steps in the ramp down region are controlled by the computer.

21 Claims, 4 Drawing Sheets

METHOD AND APPARATUS FOR PREPROGRAMMED INFUSION OF IV MEDICAMENTS

FIELD OF THE INVENTION

The present invention pertains to a system and apparatus for infusing fluid to a patient. More particularly, the present invention pertains to a programmable infusion pump which will infuse fluids to a patient in accordance with a profiled infusion regimen. The present invention is particularly, but not exclusively, useful for administering cyclic total parenteral nutrition (C-TPN).

BACKGROUND OF THE INVENTION

Cyclic total parenteral nutrition (C-TPN) is a widely used infusion therapy for providing nutrition to patients who are not able to extract nutrition from food in a normal manner. One great advantage of C-TPN is that, by concurrently infusing a solution of dextrose, amino acids and fat, the C-TPN therapy need not be continuous. Thus, this therapy permits an improved quality of life for the patient by allowing him or her to resume normal daytime activities. As implied, C-TPN is indicated for patients, both young and old, who still require long-term parenteral nutrition, but who have demonstrated they can function for extended periods of time without receiving infused fluids.

As might be expected, a cyclical therapy which is accomplished by periodically initiating and terminating IV infusions needs to be administered in a manner which allows the body's metabolic processes to properly adjust to the infusions. Such an adjustment may be necessary either at the beginning of the infusion or at the end of the infusion. C-TPN is certainly no exception. It typically happens that C-TPN requires stabilization of the body's metabolic processes at both the initiation and the termination of each infusion session in the therapy. Specifically, with C-TPN it is necessary to avoid hyperglycemia in the early stages of the infusion process, and to avoid hypoglycemia during the final stages of the process. To avoid these conditions, C-TPN is normally started with a gradual increase in the rate at which fluid is infused to the patient, and is ended with a gradual decrease in this rate.

The problems with C-TPN therapy concerning hyperglycemia and hypoglycemia have been known for some time. The general response to overcome these problems has been to somehow taper the initiation and the termination of the therapy. Indeed, several methods have been suggested for these purposes. Another problem, which has been less prominent, concerns the actual profiling of an infusion therapy regime which is optimally suited for the particular patient. For example, pediatric patients will require different infusion regimens than will adult patients. And geriatric patients may require yet another regimen. This problem is particularly acute where C-TPN is to be administered using relatively expensive infusion pumps. Each case will be different and, consequently, it may be necessary to reprofile the infusion regimen. Flexibility, then, is key.

Some apparatus and methods for accomplishing C-TPN therapy using infusion pumps have been suggested. For example, U.S. Pat. No. 4,758,799 which issued to Schoon et al. for an invention entitled "Method and Apparatus for Automatic Profiled Infusion in Cyclic TPN" establishes an infusion regimen, or cycle profile, which begins at a set starting infusion rate and which has an appropriate steady-state rate and appropriate tapers in accordance with pre-established criteria when total volume and total infusion time per cycle are entered. The disclosure of the Schoon et al. patent, however, does not address the problem confronted when a patient is unable to handle the set starting infusion rate which, as is disclosed for Schoon et al., is about 60 ml/hr. Further, the disclosure of Schoon et al. requires an upward taper and a downward taper which, other than their start and end points, are effectively identical. In short, there is little flexibility in profiling the infusion regimen. Another example, though perhaps less sophisticated than the Schoon et al. disclosure, is a method wherein the infusion rate during the tapering periods is one half the maintenance rate. Such a method is disclosed in an article entitled "Cyclic Total Parenteral Nutrition" by Bennett and Rosen, Nutrition in Clinical Practice 5:163-165, 1990.

In light of the above, it is an object of the present invention to provide a system and method for infusing C-TPN fluids to a patient which is an efficacious therapy for the patient who requires C-TPN. Another object of the present invention is to provide a system and method for infusing C-TPN fluids to a patient which is adaptable for use by either a pediatric, an adult, or a geriatric patient. Still another object of the present invention is to provide a system and method for infusing C-TPN fluids to a patient which allows the user to adjust the infusion regimen to meet the specific needs of the particular patient. Yet another object of the present invention is to provide a system and method for infusing C-TPN fluids to a patient which, with selected input data, automatically profiles an infusion regimen which insures an enhanced accuracy. Another object of the present invention is to provide a system for infusing C-TPN fluids to a patient which is simple to use, relatively easy to manufacture, and comparatively cost effective.

SUMMARY OF THE INVENTION

In accordance with the present invention, an apparatus for infusing C-TPN fluids to a patient includes a fluid source, a pump for infusing fluid from the source to a patient, and a computer operatively associated with the pump to control the infusion. Using input data as to i) the total volume of fluid to be infused, ii) the total time for infusion of this volume of fluid, and iii) the percentage of this total time to be used for ramping up to a steady-state maintenance infusion rate, the system of the present invention will profile an infusion regimen. As intended for the present invention, this infusion regimen starts from a zero infusion rate and has a ramp up region, a steady state or flat region, and a ramp down region. The ramp down region is then followed by a KVO rate of infusion, i.e. an infusion rate of approximately 1 ml/hr which is sufficient to "Keep the Vein Open" and prevent clotting. In the ramp up and ramp down regions the changes in infusion rate are accomplished in steps.

With the input data, the computer first calculates the steady state or maintenance infusion rate which will be necessary for performing the infusion regimen. This steady state infusion rate is then evaluated. If it is greater than what is generally acceptable, i.e. approximately 350 ml/hr, the user will be given an error message and the input data must be changed to indicate either less volume for infusion or more time to infuse. If the steady state infusion rate is acceptable, then a step size is selected which will be used to periodically change the rate of infusion in the ramp up and the ramp down regions of the infusion regimen. Specifically, if the steady state infusion rate is greater than 30 ml/hr, then a 5 ml/hr step size is selected. Otherwise, a 1 ml/hr step size is used.

The actual duration of the ramp up region is determined from the input data and is established as a percentage of the total time to be used for the infusion regimen. The duration of the ramp down region is taken to be the same as for the ramp up region. With these parameters the computer establishes the number of time intervals and the duration of the time intervals between step size increments in the ramp up region. More specifically, different time intervals are used between the individual steps in the ramp up region to trifurcate the ramp up operation. This is done to more accurately fit the increasing rate of infusion to an idealized constant rate of increase. It is accomplished by making the time interval which follows the initial step increment, and the time interval which precedes the final step increment approximately one and one half times longer than all of the other time intervals between steps in the ramp up region. Further, the last step increment in the ramp up region may vary from the selected step size and will take whatever value is necessary to close on the steady state infusion rate. Thus, the ramp up region is effectively trifurcated into an initial change in rate of infusion, an intermediate change in rate of infusion, and a final transitional change in rate of infusion. In any event, this ramp up region transitions the pump from an initial zero rate of infusion to the desired steady state infusion rate of the infusion regimen.

After the ramp up region of the infusion regimen has been accomplished, the infusion regimen requires the pump provide a steady state or maintenance infusion rate for that period of the total infusion time which excludes the ramp up and ramp down regions. For example, if the ramping up region was originally selected to be nine percent (9%) of the total infusion time, then the ramp down time will also be 9% of the total infusion time and the steady state region will be eighty two percent (82%) of the total infusion time. These percentages can, of course, be varied according to the input data.

Upon completion of the steady state region, the infusion regimen will require the pump to begin its ramp down. This action is initiated by a decrement from the steady state infusion rate which is equal to the last step increment in the ramp up region. Thereafter, a comparator in the computer compares the actual rate of infusion with an ideal rate of infusion. For purposes of the present invention, the ideal infusion rate is taken to be equal to twice the volume remaining to be infused, divided by the time remaining in the infusion regimen. During this comparison, whenever the difference between the actual infusion rate and the computed ideal infusion rate exceeds a certain value, the infusion rate of the pump will be further decremented by the previously selected step size. The last decrement in the ramp down region will be whatever is necessary to have the pump maintain a KVO rate of infusion.

In accordance with the present invention, in the event there is no data input for the percentage of total infusion time which is to be used for ramping up, the computer in the pump will default to a ramp up time which is equal to eight percent (8%) of the total time for infusing fluids to the patient. In an alternate embodiment for the present invention, the ramp up time can be set for a time certain. For example, the ramp up region can be set to last for one hour. In each case, for the alternate embodiment, the ramp down region will also be set for the same time certain as was selected for the ramp up region. The remaining calculations and features of the alternate embodiment will then be substantially the same as for corresponding calculations and features of the preferred embodiment.

The novel features of this invention, as well as the invention itself, both as to its structure and its operation will be best understood from the accompanying drawings, taken in conjunction with the accompanying description, in which similar reference characters refer to similar parts, and in which:

DESCRIPTION OF THE PREFERRED EMBODIMENTS

Figure 1:
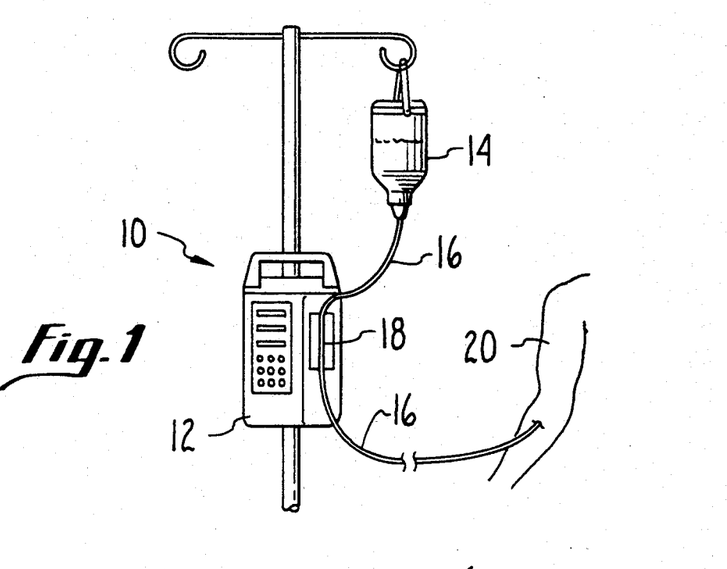
FIG. 1 is an elevational view of the system of the present invention shown operationally connected to a patient.

Referring initially to FIG. 1, a system for administering cyclic total parenteral nutrition (C-TPN) is shown and is generally designated 10. As shown, this system 10 includes a programmable pump 12 which is useful for pumping fluid from a fluid source 14 through an IV line 16. More specifically, the pump 10 includes a pumping mechanism 18 which is operatively connected to the IV line 16 for infusing TPN fluid from the fluid source 14 to a patient 20. As intended for the system 10 of the present invention, pump 12 can be either a peristaltic pump or a volumetric pump. In any case, pump 12 must include a computer or a programmable means which is capable of controlling the pump 12 for the infusion of TPN fluids from the fluid source 14 to the patient 20 in accordance with the operational parameters disclosed herein.

Figure 2:
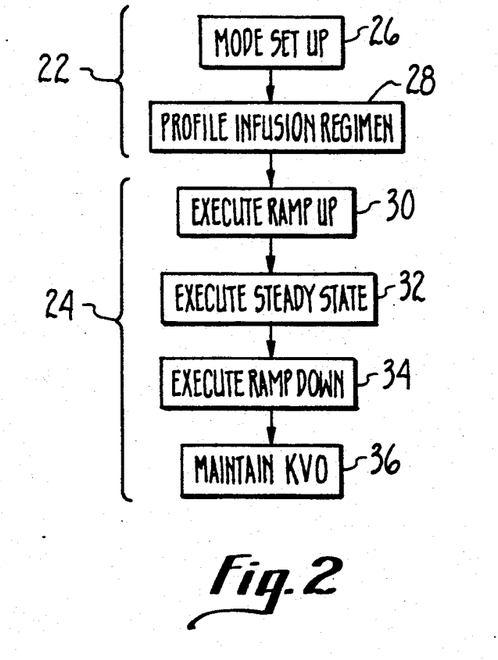
FIG. 2 is a functional diagram showing generalized sequential steps in the operation of the present invention.
Figure 3:
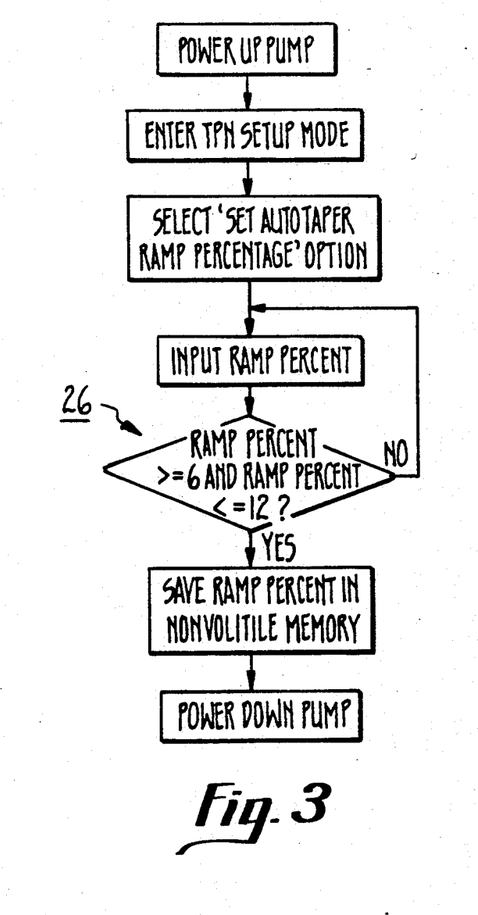
FIG. 3 is a logic flow chart for the mode set up of the system of the present invention.
Figure 4:
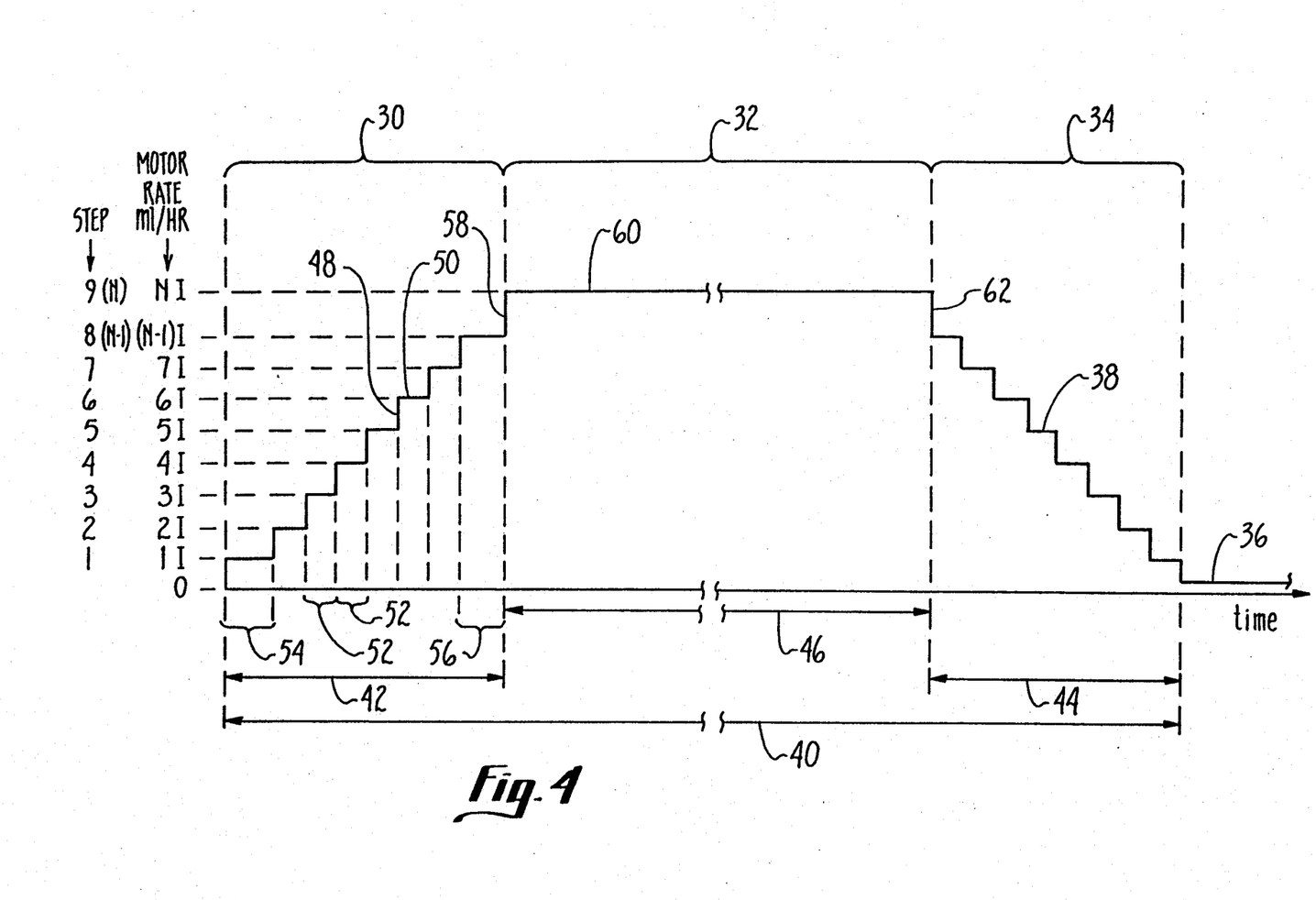
FIG. 4 is a graph of an infusion regimen for infusion of TPN fluids in accordance with the present invention.

In FIG. 2 it will be seen that the overall operation of the system 10 includes a manual operation portion 22 and an automatic operation portion 24. More specifically, the manual operation portion 22 includes both a mode set up activity which is indicated at block 26, and a profile function which together with manual operation establish parameters for the infusion regimen of the present invention. This profile function is indicated at block 28. For cross referencing purposes, the mode set up activity 26 is generally shown in FIG. 3, and the profiling function 28 is generally shown in the logic flow chart of FIG. 5A. Also for cross referencing purposes, it is to be appreciated that FIG. 4 presents the graph 38 of a typical infusion regimen which includes the ramp up region 30, the steady state region 32, the ramp down region 34, and the KVO state 36 which correspond directly with the respective blocks shown in FIG. 2. Further, the interrelationship of logic operations for the ramp up region 30, the steady state region 32, the ramp down region 34, and the KVO state 36 is shown in FIG. 5B.

Returning now to FIG. 3, it will be seen that pump 12 can be preset for a particular mode of operation. Specifically, after pump 12 has been powered up and proper entries have been made to indicate the pump 12 is to be used for TPN, the ramp up percentage can be selected. Preferably, as indicated in FIG. 3, the ramp up percentage will be selected in the range of from six to twelve percent (6%-12%) of the total time 40 for infusion regimen. In the event the user inadvertently fails to enter a ramp up percentage, a default value of eight percent (8%) can be used for ramp up region 30. Alternatively, a time certain for ramp up region 30 (e.g. one hour) may be selected at this point. In any event, the computer or programmable means in pump 10 is manually or automatically programmed with input data with which a time for ramp up region 30 can be determined. Additional input data is, of course, also needed. Specifically, along with the data setting the ramp up percentage, it will also be necessary to input the total volume of fluid to be infused and the total time to be used for the infusion regimen. Just how all of this input data is used to profile the infusion regimen for the system 10 of the present invention is best seen by cross referencing FIG. 4 and FIG. 5A.

Figure 5A:
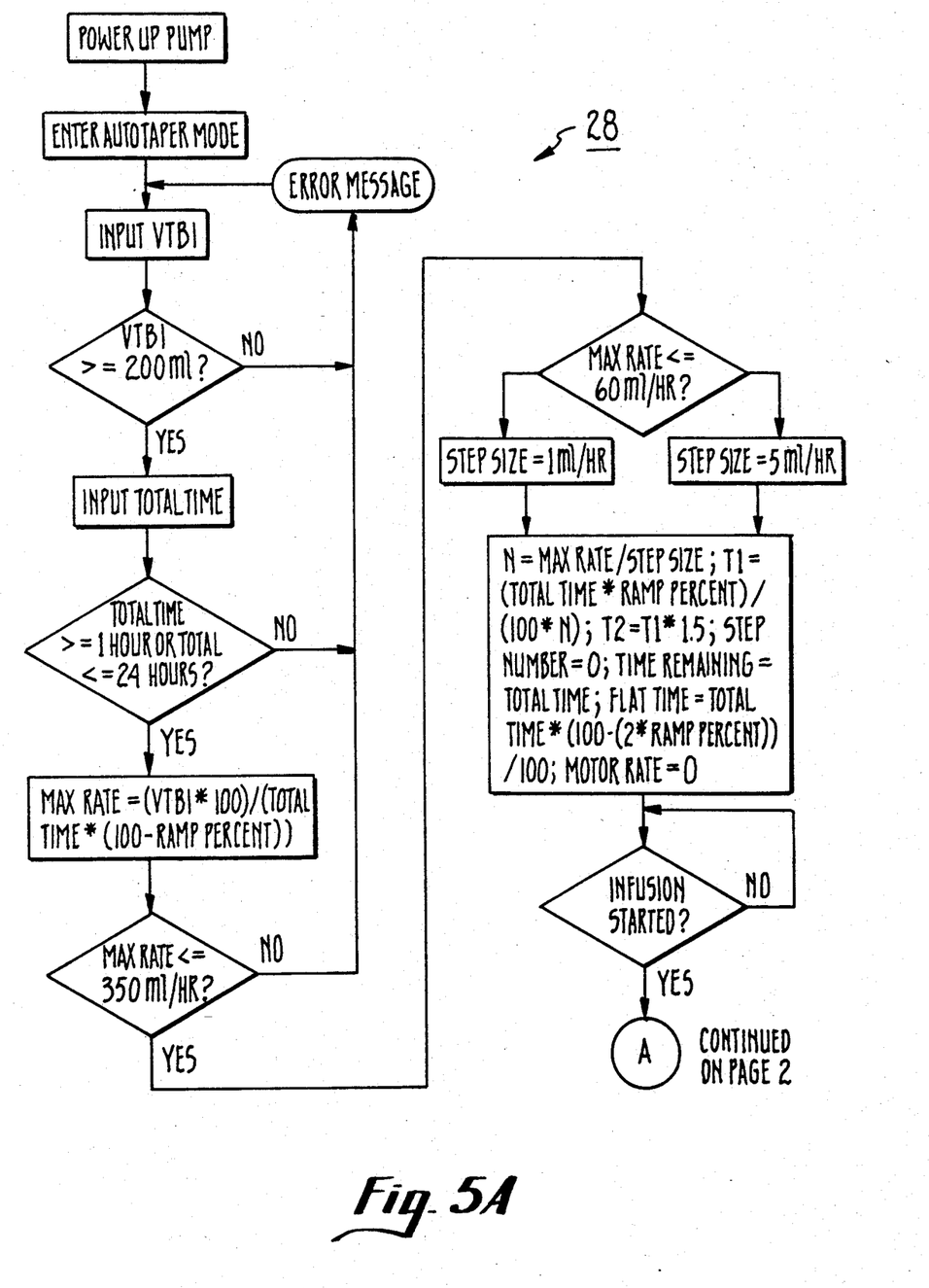
FIG. 5A is a logic flow chart showing the steps for profiling the infusion regimen using selected input data.
Figure 5B:
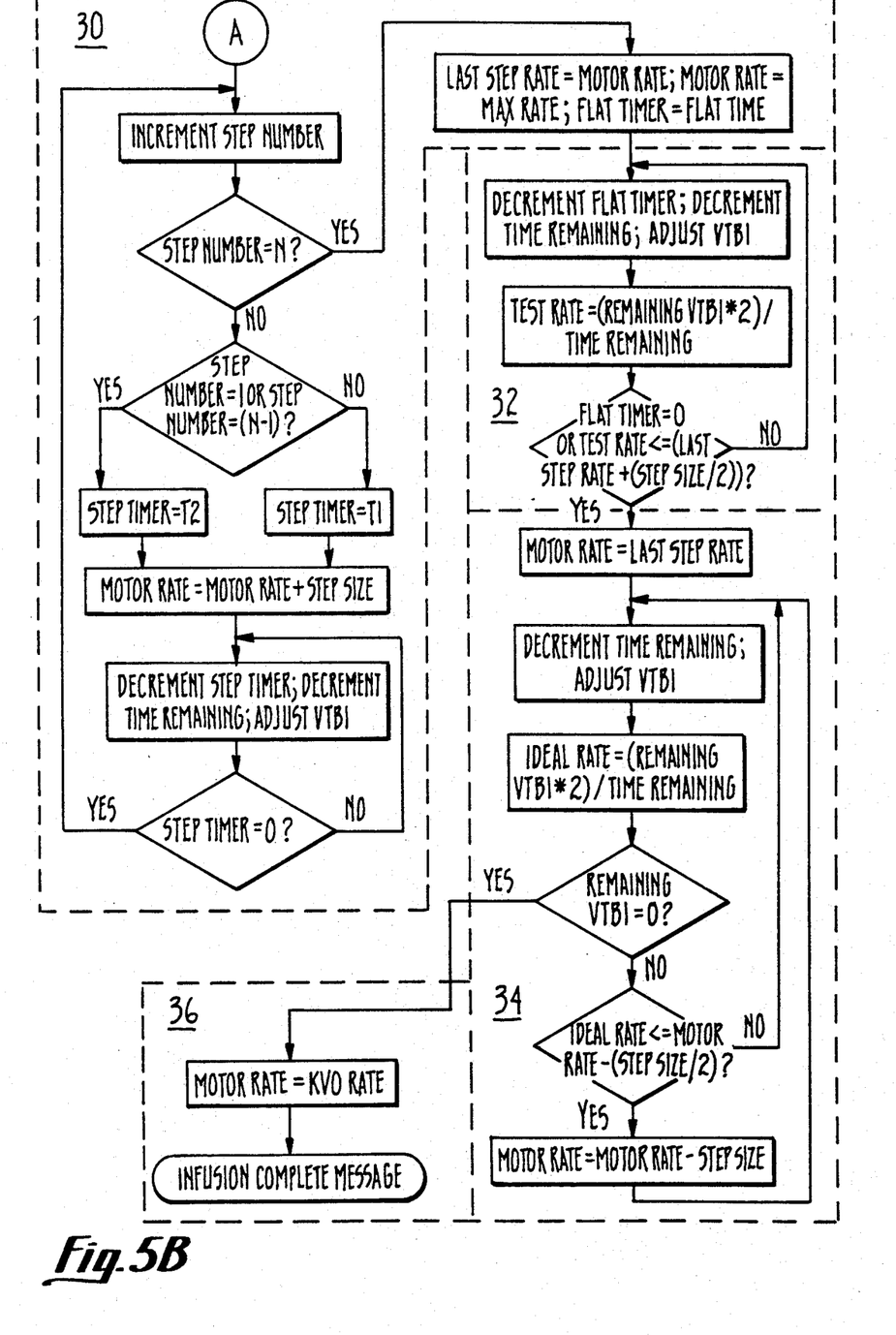
FIG. 5B is a continuation of the logic flow chart in FIG. 5A showing the steps for executing the ramp up region, the steady state region, and the ramp down region of the infusion profile in accordance with the present invention.

Profiling the infusion regimen is accomplished by following the logic operations set forth in FIG. 5A. There it will be seen that the user must initially program pump 12 by entering the volume to be infused (VTBI) and the total time 40 for the infusion. In FIG. 4, these variables are graphically represented respectively as the area under the curve of graph 38, and as the time line 40. Further, in FIG. 5A it is indicated that these variables should fall within certain established limits. Specifically, the VTBI should be greater than or equal to two hundred milliliters (VTBI>=200 ml), and the total time for infusion should be between one and twenty four hours (1-24 hrs). These limitations can be changed as desired and, though somewhat arbitrary, they have been chosen here because of their general acceptance as operational parameters in the pertinent art. In any event, once the values for these variables have been chosen, system 10 then automatically profiles the graph 38 in FIG. 4.

Graph 38 in FIG. 4 shows an actual infusion profile as generated for the system 10 of the present invention. An idealized graph would, however, be depicted as a straight-line steady increase in the infusion rate in the ramp up region 30 during a ramp up time period 42. This ramp up 30 would then be followed by a flat steady state infusion rate in the steady state region 32 for a steady state time period 46. And the steady state region 32 would, in turn, be followed by a straight-line steady decrease in the infusion rate during a ramp down time period 44 for the ramp down region 34. Practical matters, however, make it more feasible to increase and decrease infusion rates in step increments during ramp up 30 and in step decrements during ramp down 34. Fortunately, there is no loss in efficacy for the TPN therapy using this approach.

Referring for the moment to FIG. 4, it will be seen that each step increment in the ramp up region 30 is defined by a step size 48 and a subsequent time interval 50 which immediately follows the step size 48. As expected, the magnitudes of both the step size 48 and the time interval 50 are directly related to the VTBI and to the total time 40 for the infusion regimen. Therefore, to precisely establish these steps in the ramp up region 30, the system 10 of the present invention first calculates a steady state infusion rate 60. As an aside, this steady state infusion rate 60 is also referred to herein as the max rate, or the maintenance rate, and these terms are to be considered interchangeable. Conceptually, the steady state infusion rate 60 for the infusion regimen is calculated using simple geometrical relationships from the idealized graph for an infusion regimen as described above. Using this approach, the maintenance rate 60 is determined by dividing the VTBI by a number which is equal to the total time 40 required for the infusion regimen, less the ramp up time 42. FIG. 5A shows that if the resultant steady state infusion rate 60 is calculated to be greater than three hundred and fifty milliliters per hour (350 ml/hr), system 10 will display an error message. The user operator must then again input a VTBI, or a total time 40, which will bring the steady state infusion rate 60 below the 350 ml/hr level. FIG. 5A further shows that with a max rate 60 less than 350 ml/hr, step size 48 for increments (I) in the ramp up region 30 will be set at five milliliters per hour (5 ml/hr) unless the max rate is less than or equal to sixty milliliters per hour (60 ml/hr). In the event the max rate is equal to or less than 60 ml/hr, step size 48 for increments in the ramp up region 30 will then be set at one milliliter per hour (1 ml/hr).

Having already calculated a max rate 60, and having selected an increment (I) for step size 48, it is a simple matter to divide the max rate 60 by the selected step size 48 in order to calculate the number of steps (N) which will be required to complete the ramp up 30 from an initial infusion rate of zero ml/hr to the max rate 60. Note here that N will always be a whole number, and that the product of N times the selected step size (I) will be less than or equal to the max rate 60. Now, the time intervals 50 must be determined.

Actually, the time intervals 50 in ramp up region 30 may have either one of two values. It has been determined that a sufficiently close approximation to an idealized straight-line steady increase in infusion rate during ramp up 30 can be accomplished by having all of the intermediate time intervals 52 be individually shorter in duration than either the initial time interval 54 or the final time interval 56. Specifically, the initial time interval 54 and the last time interval 56 in ramp up region 30 are set to be equal to each other and are given a value of T2 which is one and one half times longer than the time T1 of the intermediate time intervals 52.

The execution of ramp up region 30 is accomplished by following the logic steps set out for the ramp up region 30 in FIG. 5B. As shown, the first action in this operation is to determine which one of the N number of steps in ramp up 30 is to be performed. A modulo counter is incorporated for this purpose and, although FIG. 5B indicates a process for counting up from one to N, it is equally possible to count down from N to zero. Nevertheless, for the procedure as shown, if the counter is not at N, an inquiry is made as to whether this is either the first or the penultimate step in the ramp up. If the answer to this inquiry is "yes", then a time interval value of T2 is used to follow the step increment. Otherwise, a time interval value of T1 is used. To actually perform the step, the infusion rate for pump 12 is incremented by one step size 48 (e.g. either 5 ml/hr or 1 ml/hr) and a step timer is then decremented down from the appropriate value of either T1 or T2. This continues through the ramp up region 30 until the penultimate step. As indicated above, the time interval following the penultimate step is set for a time value of T2. Further, the last step increment 58 in ramp up 30 may vary from the selected step size 48. As intended, this last step increment 58 will take whatever value is necessary to close on the steady state infusion rate 60. Throughout the ramp up 30, the VTBI is adjusted so that at any particular time the remaining VTBI is known.

In the above described manner, ramp up region 30 is effectively trifurcated to create an initial change in rate of infusion which is established by a single step size increment 48 which is held over time interval 54 for a time T2. This is followed by an intermediate change in rate of infusion which includes a sequence having a plurality of steps. Specifically, each step in this sequence is established by a step size increment 48 which is held over a time interval 52 for a time T1. A final change in the infusion rate is made during ramp up 30 by holding the penultimate N-1 step for a final time interval 56 of T2. The purpose of all this is to more closely fit the real ramp up 30 to an idealized straight-line steadily increasing rate of infusion during this part of the operation of system 10.

Cross referencing FIG. 5B with FIG. 4 also shows that the steady state region 32 is maintained with pump 12 infusing fluid at the max rate 60 as the time 46 for steady state infusion is being decremented. Also, during the time 46 the VTBI is being adjusted. Specifically, during operation in the steady state region 32 a test rate is periodically calculated and this test rate is compared with a desired value. More specifically, the test rate is calculated as twice the volume remaining to be infused divided by the total time 40 remaining (i.e. time remaining for steady state time 46 and the total of the ramp down time 44). If this test rate is less than or equal to the sum of the max rate 60 plus one half step size increment 48, or if the steady state time 46 remaining is zero, then the system 10 begins to ramp down 38.

Like ramp up 30, ramp down 34 is accomplished in steps. The operation for accomplishing ramp down 34, however, is quite different than the operation described above for ramp up 30. In effect, ramp down 34 is feed back controlled to change the actual rate of infusion in accordance with a calculated ideal rate of infusion. Just how this is done for the preferred embodiment of the present invention is best seen by cross referencing the ramp down region 34 shown in FIG. 5B with the corresponding region of graph 38 in FIG. 4.

Initiation of the ramp down 34 is done by decreasing the max rate of infusion 60 by an amount equal to the last step increment 58 used in ramp up region 30. Thus, the initial step decrement 62 in the ramp down region 34 is equal to the last step increment 58 in the ramp up region 30. As will be readily appreciated by the skilled artisan, this leaves N-1 steps which can be decremented with a step size 48 change during ramp down 38.

An ongoing process throughout the infusion profile has been the monitoring of the remaining VTBI. Using this remaining VTBI and the time remaining in the ramp down region 34, an ideal infusion rate is calculated. Specifically, and again using elementary geometric relationships, the ideal infusion rate during ramp down 34 is calculated to be equal to twice the VTBI divided by the time remaining in the infusion profile. This ideal infusion rate is then compared by a comparator in system 10 with the actual infusion rate being generated by the pump 12. As long as there is a remaining VTBI, pump 12 will continue at it last infusion rate until the calculated ideal infusion rate falls below a set value. Specifically, the infusion rate of the pump 12 will be decremented by an amount equal to a step size 48 whenever the calculated ideal infusion rate is less than or equal to the value of the actual infusion rate minus one half of step size 48. As indicated in FIG. 5B, these iterations continue until VTBI is equal to zero. The actual connections between the programmable computer of the pump 12 and the pumping mechanism of the pump 12 which accomplish the controlled reduction in infusion rate during ramp down 34 can be made in any manner well known in the pertinent art. The present invention recognizes many variations in such connections are possible and no attempt is made here is select one feed back system over any other such system.

Upon completion of ramp down 34, system 10 goes into a KVO state 36. As mentioned above, the KVO rate can be set as desired but is preferably n the order of 1 ml/hr.

While the particular C-TPN system for infusing fluids to a patient as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

We claim:

1. A system for infusing a fluid to a patient which comprises:
    a fluid source;
    means connected to said fluid source for pumping fluid from said fluid source to said patient;
    programmable means connected to said pumping means for operating said pumping means in accordance with an infusion regimen, said infusion regimen having a flat steady state infusion rate with a ramp up change in infusion rate which includes an initial change in rate of infusion, an intermediate change in rate of infusion, and a final transitional change in rate of infusion to begin said regimen, and a controlled ramp down change in infusion rate to end said regimen; and
    input means connected to said programmable means for profiling said infusion regimen to compatibly control said programmable means with input data including a total volume of said fluid to be infused and a total time for infusing said total volume of fluid.

2. A system as recited in claim 1 wherein said ramp up change in infusion rate and said ramp down change in infusion rate are accomplished in steps, said steps in said ramp up change in infusion rate being characterized by a step size increment which is held for a determinable time interval, and said steps in said ramp down change in infusion rate being characterized by a step size decrement which is held for a controlled time interval.

3. A system as recited in claim 2 wherein said time interval for steps in said initial and said transitional changes in rate of infusion are substantially equal to each other and are directly related to said time interval for steps in said intermediate change in rate of infusion.

4. A system as recited in claim 3 wherein said intermediate change in rate of infusion is directly related to said total time for infusing fluid to said patient.

5. A system as recited in claim 3 wherein said intermediate change in rate of infusion is directly related to a time certain.

6. A system as recited in claim 3 wherein said time intervals for steps in said initial and said transitional changes are approximately one and one half times longer in duration than said time intervals for steps in said intermediate change.

7. A system as recited in claim 2 wherein said step size increment in said ramp up change and said step size decrement in said ramp down change are established by said input data for volume to be infused, said step size being approximately equal to five milliliters per hour (5 ml/hr) when said steady state infusion rate exceeds a set value of 30 ml/hr and being approximately equal to one milliliter per hour (1 ml/hr) when said steady state infusion rate is equal to or lower than said set values.

8. A system as recited in claim 2 wherein said ramp up change in infusion rate begins at zero.

9. A system as recited in claim 2 wherein said ramp down infusion rate transitions from said steady state infusion rate to an infusion rate of approximately one milliliter per hour (1 ml/hr), and said system further comprises means for operating said pumping means at said infusion rate of approximately one milliliter per hour (1 ml/hr) after completion of said infusion regimen.

10. A system as recited in claim 9 wherein said programmable means further comprises:
   means for monitoring said pumping means to determine an actual rate of infusion of fluids from said fluid source;
   means for monitoring a remaining volume of fluid to be infused;
   means for determining the time remaining for completion of said infusion regimen;
   means for calculating an ideal infusion rate using information on said remaining volume to be infused and said time remaining for completion of said infusion regimen;
   a comparator for determining the difference between said ideal infusion rate and said actual rate; and
   means for implementing a step size decremental change in said infusion rate whenever said difference between said ideal infusion rate and said actual rate exceeds a predetermined value.

11. A system as recited in claim 10 wherein said predetermined value is equal to one half said step size.

12. A system as recited in claim 11 wherein said ramp up change in infusion rate begins at zero.

13. An apparatus for infusing fluids to a patient from a fluid source which comprises:
   a pump connected with said fluid source to pump fluid therefrom; and
   a computer, said computer being programmable to control said pump for infusion of fluids to said patient in accordance with a profiled infusion regimen, said regimen including a volume of fluid to be infused to the patient, a time for infusing said volume, and a ramp up infusion region having interrelated incremental rates of infusion which include an initial change in rate of infusion, an intermediate change in rate of infusion, and a final transitional change in rate of infusion which transition said pump from zero rate of infusion to a steady state rate of infusion.

14. An apparatus as recited in claim 13 wherein said profiled infusion regimen further includes a ramp down region controlled by said computer in which infusion rates are decremented from said steady state rate of infusion based on remaining volume of fluid to be infused to the patient and remaining time for infusing said remaining volume.

15. An apparatus as recited in claim 14 wherein said ramp up region and said ramp down region are accomplished in steps, said steps in said ramp up region being characterized by a step size increment which is held for a determinable time interval, and said steps in said ramp down region being characterized by a step size decrement which is held for a controlled time interval, and wherein said step size increment in said ramp up region and said step size decrement in said ramp down region are established by said profiled infusion regimen for volume to be infused, said step size being approximately equal to five milliliters per hour (5 ml/hr) when said steady state infusion rate exceeds a set value of 30 ml/hr and being approximately equal to one milliliter per hour (1 ml/hr) when said steady state infusion rate is equal to or lower than said set value.

16. An apparatus as recited in claim 15 wherein said time interval for steps in said initial and said transitional changes in said ramp up region are substantially equal to each other and are approximately one and one half times longer in duration than said time intervals for steps in said intermediate change and further wherein said time intervals for steps in said intermediate change in rate of infusion are directly related to said time for infusing said volume of fluid to said patient.

17. An apparatus as recited in claim 14 wherein said computer further comprises: means for monitoring said pumping means to determine an actual rate of infusion of fluids from said fluid source; means for monitoring said remaining volume of fluid to be infused to the patient; means for determining the remaining amount of said time for infusing said volume of said fluid for completion of said infusion regimen; means for calculating an ideal infusion rate using information on said remaining volume to be infused and said time remaining for completion of said infusion regimen; a comparator for determining the difference between said ideal infusion rate and said actual rate; and means for implementing a step size detrimental change in said infusion rate whenever said difference between said ideal infusion rate and said actual rate exceeds a predetermined value.

18. An apparatus as recited in claim 17 wherein said predetermined value is equal to one half said step size.

19. A method for administering total parenteral nutrition to a patient with a programmable pump in accordance with an infusion regimen based on a selected volume of fluid to be infused and a total time for infusion, which comprises the steps of:
   selecting times in said infusion regimen for a ramp up region, a steady state region, and a ramp down region, each said region being established as a percentage of said total time for infusion;
   inputing data to said pump for said volume to infused and said total time for infusion;
   calculating a steady state infusion rate;
   selecting a step size compatible with said steady state infusion rate for use as increments in said ramp up region and decrements in said ramp down region;

selecting different time intervals in said ramp up region, between said step size increments, to transition operation of said pump from a zero infusion rate to said steady state infusion rate;

maintaining said steady state infusion rate in said steady state region of operation;

entering said ramp down region with one said step size decrement in said rate of infusion;

calculating an ideal infusion rate during operation in said ramp down region;

comparing an actual infusion rate with said ideal infusion rate to determine a difference therebetween;

reducing said actual infusion rate by one step size decrement when said difference exceeds a certain value; and operating said pump at a KVO rate after operation in said ramp down region is completed.

20. A method as recited in claim 19 wherein said ideal infusion rate is calculated during said ramp down operation using a remaining volume to be infused and a remaining time for infusing said volume.

21. A method as recited in claim 19 wherein said step size is five milliliters per hour (5 ml/hr) when said steady state infusion rate is greater than thirty milliliters per hour, and is one milliliter pr hour (1 ml/hr) when said steady state infusion rate is less than or equal to thirty milliliters per hour.

* * * * *